United States Patent [19]
Tsai et al.

[11] Patent Number: 6,078,386
[45] Date of Patent: *Jun. 20, 2000

[54] INSPECTION SYSTEM SIMULTANEOUSLY UTILIZING MONOCHROMATIC DARKFIELD AND BROADBAND BRIGHTFIELD ILLUMINATION SOURCES

[75] Inventors: Bin-Ming Benjamin Tsai, Saratoga; Russell M. Pon, Santa Clara, both of Calif.

[73] Assignee: KLA Instruments Corporation, San Jose, Calif.

[ * ] Notice: This patent is subject to a terminal disclaimer.

[21] Appl. No.: 09/114,427

[22] Filed: Jul. 13, 1998

Related U.S. Application Data

[62] Division of application No. 08/884,467, Jun. 27, 1997, Pat. No. 5,822,055, which is a continuation of application No. 08/489,019, Jun. 6, 1995.

[51] Int. Cl.[7] .............................. G01N 21/00; G01B 11/00
[52] U.S. Cl. ...................... 356/237.1; 356/394; 356/239
[58] Field of Search ................................... 356/237, 239, 356/394

[56] References Cited

U.S. PATENT DOCUMENTS 5,822,055  10/1998  Tsai et al. ............................... 356/237

*Primary Examiner*—Robert H. Kim
*Attorney, Agent, or Firm*—Allston L. Jones

[57] ABSTRACT

A method and inspection system to inspect a first pattern on a specimen for defects against a second pattern that is intended to be the same where the second pattern has known responses to at least one probe. The inspection is performed by applying at least one probe to a point of the first pattern on the specimen to generate at least two responses from the specimen. Then the first and second responses are detected from the first pattern, and each of those responses is then compared with the corresponding response from the same point of the second pattern to develop first and second response difference signals. Those first and second response difference signals are then processed together to unilaterally determine a first pattern defect list.

24 Claims, 13 Drawing Sheets

INSPECTION SYSTEM SIMULTANEOUSLY UTILIZING MONOCHROMATIC DARKFIELD AND BROADBAND BRIGHTFIELD ILLUMINATION SOURCES

This is a divisional of application(s), Ser. No. 08/884,467, filed Jun. 27, 1997, now U.S. Pat. No. 5,822,055 which in turn was a continuation of Ser. No. 08/489,019 filed on Jun. 6, 1995.

FIELD OF THE INVENTION

The field of the present invention is optical inspection of specimens (e.g., semiconductor wafers), more specifically, probing a specimen to create at least two independent optical responses from the specimen (e.g., brightfield and darkfield reflections) with those responses being considered in conjunction with each other to determine the occurrence of defects on or in the specimen.

BACKGROUND OF THE INVENTION

In the past there have been three techniques for optically inspecting wafers. Generally they are brightfield illumination, darkfield illumination and spatial filtering.

Broadband brightfield is a proven technology for inspecting pattern defects on a wafer with the broadband light source minimizing contrast variations and coherent noise that is present in narrow band brightfield systems. The most successful example of such a brightfield wafer inspection system is the KLA Model 2130 (KLA Instruments Corporation) that can perform in either a die-to-die comparison mode or a repeating cell-to-cell comparison mode. Brightfield wafer inspection systems, however, are not very sensitive to small particles.

Under brightfield imaging, small particles scatter light away from the collecting aperture, resulting in a reduction of the returned energy. When the particle is small compared to the optical point spread function of the lens and small compared to the digitizing pixel, the brightfield energy from the immediate areas surrounding the particle usually contribute a lot of energy, thus the very small reduction in returned energy due to the particle size makes the particle difficult to detect. Further, the small reduction in energy from the small particle is often masked out by reflectivity variations of the bright surrounding background such that small particles cannot be detected without a lot of false detections. Also, if the small particle is on an area of very low reflectivity, which occurs for some process layers on wafers and always for reticles, photomasks and flat panel displays, the background return is already low thus a further reduction due to the presence of a particle is very difficult to detect.

Many instruments currently available for detecting small particles on wafers, reticles, photo masks, flat panels and other specimens use darkfield imaging. Under darkfield imaging, flat, specular areas scatter very little signal back at the detector, resulting in a dark image, hence the term darkfield. Meanwhile, any presence of surface features and objects that protrude above the surface scatter more light back to the detector. In darkfield imaging, the image is normally dark except areas where particles, or circuit features exist.

A darkfield particle detection system can be built based on the simple assumption that particles scatter more light than circuit features. While this works well for blank and unpatterned specimens, in the presence of circuit features it can only detect large particles which protrude above the circuit features. The resulting detection sensitivity is not satisfactory for advanced VLSI circuit production.

There are instruments that address some aspects of the problems associated with darkfield. One instrument, by Hitachi, uses the polarization characteristics of the scattered light to distinguish between particles and normal circuit features. This is based on the assumption that particles depolarize the light more than circuit features during the scattering process. However, when the circuit features become small, on the order of, or smaller than, the wavelength of light, the circuit can depolarize the scattered light as much as particles. As a result, only larger particles can be detected without false detection of small circuit features.

Another enhancement to darkfield, which is used by Hitachi, Orbot and others, positions the incoming darkfield illuminators such that the scattered light from circuit lines oriented at 0°, 45° and 90° are minimized. While this works on circuit lines, the scattering light from corners are still quite strong. Additionally, the detection sensitivity for areas with dense circuit patterns has to be reduced to avoid the false detection of corners.

Another method in use today to enhance the detection of particles is spatial filtering. Under plane wave illumination, the intensity distribution at the back focal plane of a lens is proportional to the Fourier transform of the object. Further, for a repeating pattern, the Fourier transform consists of an array of light dots. By placing a filter in the back focal plane of the lens which blocks out the repeating light dots, the repeating circuit pattern can be filtered out and leave only non-repeating signals from particles and other defects. Spatial filtering is the main technology employed in wafer inspection machines from Insystems, Mitsubishi and OSI.

The major limitation of spatial filtering based instruments is that they can only inspect areas with repeating patterns or blank areas. That is a fundamental limitation of that technology.

In the Hitachi Model IS-2300 darkfield spatial filtering is combined with die-to-die image subtraction for wafer inspection. Using this technique, non-repeating pattern areas on a wafer can be inspected by the die-to-die comparison. However, even with die-to-die comparison, it is still necessary to use spatial filtering to obtain good sensitivity in the repeating array areas. In the dense memory cell areas of an wafer, the darkfield signal from the circuit pattern is usually so much stronger than that from the circuit lines in the peripheral areas that the dynamic range of the sensors are exceeded. As a result, either small particles in the array areas cannot be seen due to saturation, or small particles in the peripheral areas cannot be detected due to insufficient signal strength. Spatial filtering equalizes the darkfield signal so that small particles can be detected in dense or sparse areas at the same time.

There are two major disadvantages to the Hitachi darkfield/spatial filtering/die-to-die inspection machine. First, the machine detects only particle defects, no pattern defects can be detected. Second, since the filtered images are usually dark without circuit features, it is not possible to do an accurate die-to-die image alignment, which is necessary for achieving good cancellation in a subtraction algorithm. Hitachi's solution is to use an expensive mechanical stage of very high precision, but even with such a stage, due to the pattern placement variations on the wafer and residual errors of the stage, the achievable sensitivity is limited roughly to particles that are 0.5 μm and larger. This limit comes from the alignment errors in die-to-die image subtraction.

Other than the activity by Hitachi, Tencor Instruments (U.S. Pat. No. 5,276,498), OSI (U.S. Pat. No. 4,806,774) and IBM (U.S. Pat. No. 5,177,559), there has been no interest in a combination of brightfield and darkfield techniques due to a lack of understanding of the advantages presented by such a technique.

All of the machines that are available that have both brightfield and darkfield capability, use a single light source for both brightfield and darkfield illumination and they do not use both the brightfield and the darkfield images together to determine the defects.

The conventional microscope that has both brightfield and darkfield illumination, has a single light source that provides both illuminations simultaneously, thus making it impossible to separate the brightfield and darkfield results from each other.

In at least one commercially available microscope from Zeiss it is possible to have separate brightfield and darkfield illumination sources simultaneously, however, there is a single detector and thus there is no way to separate the results of the brightfield and darkfield illumination from each other. They simply add together into one combined full-sky illumination.

It would be advantageous to have a brightfield/darkfield dual illumination system where the advantages of both could be maintained resulting in a enhanced inspection process. The present invention provides such a system as will be seen from the discussion below. In the present invention there is an unexpected result when brightfield and darkfield information is separately detected and used in conjunction with each other.

SUMMARY OF THE INVENTION

The present invention provides a method and inspection system to inspect pattern on a specimen for defects using at least two optical responses therefrom. To perform that inspection the first pattern is compared to a second pattern that has been caused to produce the same at least two optical responses. To perform the inspection, the same point on the specimen is caused to emit at least two optical responses. Each of those optical responses (e.g., darkfield and brightfield images) are then separately detected, and separately compared with the same responses from the same point of the second pattern to separately develop difference signals for each of the types of optical responses. Then those separately difference signals are processed to unilaterally determine a first pattern defect list.

That first pattern defect list can then be carried a step further to identify known non-performance degrading surface features and to exclude them from the actual defect list that is presented to the system user.

Another variation is to introduce additional probes to produce more than two optical responses from the specimen to further refine the technique to determine the defect list.

Additionally, if the specimen permits transmitted illumination, optical response detection systems can be include below the specimen to collect each of the transmitted responses to further refine the defect list and to include defects that might be internal to the specimen.

BRIEF DESCRIPTION OF THE FIGURES

FIG. 5b is a block diagram of the defect detector shown in FIG. 5a.

DESCRIPTION OF THE PREFERRED EMBODIMENT

Historically, the majority of defect inspection machines perform using either brightfield or darkfield illumination, not both. Thus the typical prior art machines are as shown in FIG. 1 with either brightfield or darkfield illumination.

Figure 1:
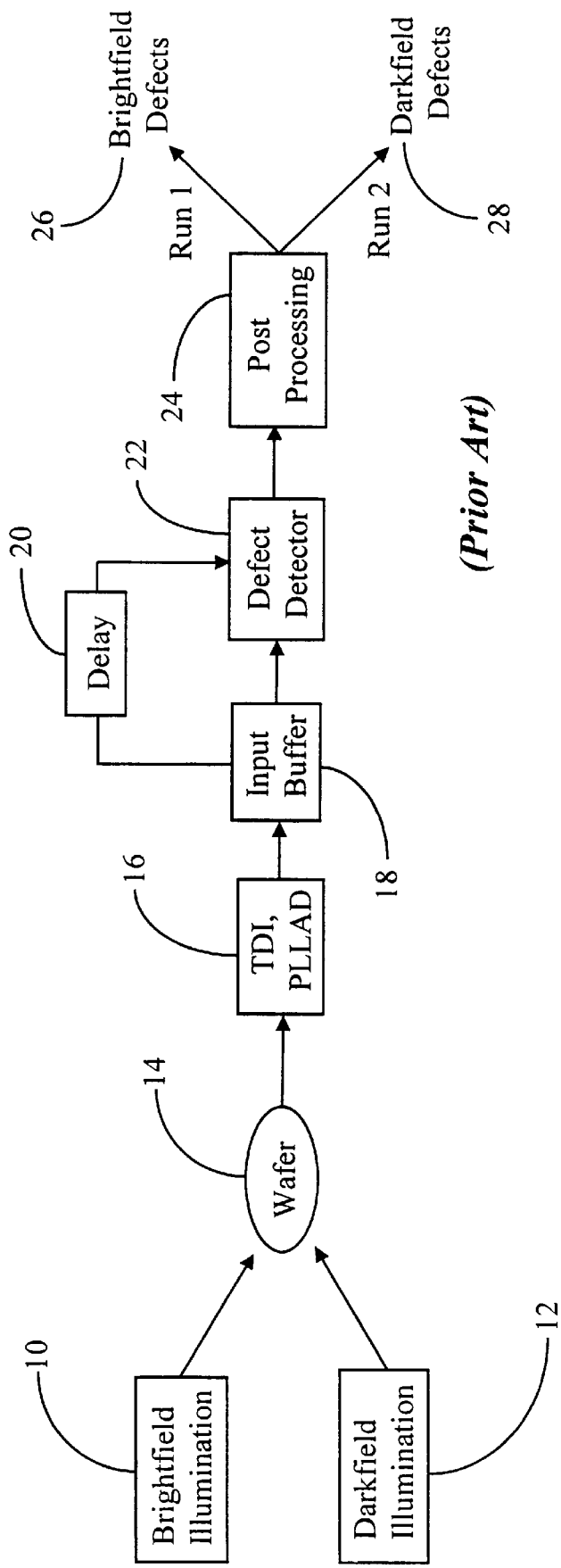
FIG. 1 is a block diagram of a prior art inspection system that performs brightfield or darkfield inspection of a wafer serially using a single signal processing channel.

In the system of FIG. 1, wafer 14 is illuminated by the appropriate brightfield or darkfield light source 10 or 12, respectively. During operation, sensor 16, shown here as a TDI (time delay integration) with PLLAD (Phase Locked Loop Analog to Digital conversion), captures the image from wafer 14 and loads a signal representative of that image into input buffer 18, (e.g., RAM). From buffer 18 the data is fed to defect detector 22 where the data from the sample being inspected is compared to a similar sample or reference wafer under control of delay 20 which provides the timing to allow for the die-to-die or cell-to-cell comparison by defect detector 22. The data from defect detector 22 is then applied to post processor 24 where the sizing and locating of the defects is performed to generate a defect list with a defect threshold value (e.g., KLA Instruments Models 2111, 2131 are such brightfield inspection machines).

If the machine of FIG. 1 were to be modified to perform both brightfield and darkfield inspection with separate brightfield and darkfield results, which is not currently done by any available inspection machine, one obvious way to perform the brightfield and darkfield functions would be to perform those functions serially with no interaction between the data of each run. In one run a light source would be employed to provide brightfield illumination 10, and in another run a light source would provide darkfield illumination 12. Assuming that brightfield illumination was used in the first run as described above for a currently available brightfield inspection system, in a subsequent run, wafer 14 could be illuminated with darkfield illumination 12 and sensor 16 would then image the darkfield image of wafer 14 which is then operated on by buffer 18, delay 20, defect detector 22 and post processor 24 as was the brightfield image to create a darkfield defect list 28 with post processor 24 separately generating a darkfield defect threshold value.

Thus, image points on wafer 14 that correspond to a data point in the brightfield defect list 26 has a value that exceeds the brightfield defect threshold value resulting in that point on wafer 14 being identified as including a defect. Separately, and using the same operational technique, the darkfield defect list values that exceed the darkfield defect threshold correspond to points on wafer 14 being identified as being occupied by a defect. Therefore, it is entirely possible that points on wafer 14 may be identified as being occupied by a defect by one of the brightfield and darkfield imaging and not both, and possibly by both. Thus, post processor 24 would provide two individual, uncorrelated, defect lists, one of defects detected using brightfield illumination 10 and the second using darkfield illumination 12.

Figure 2B:
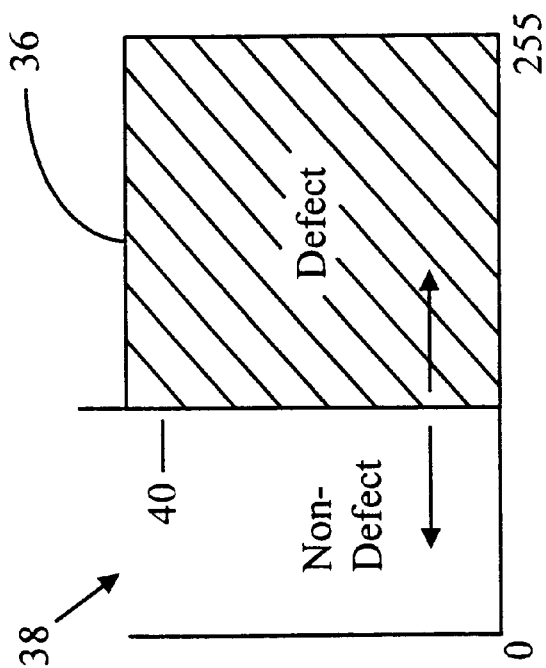
FIG. 2b is a graph of the results of a prior art darkfield inspection wherein a threshold level is determined and all signals having a signal above that value are classified as defects.
Figure 2A:
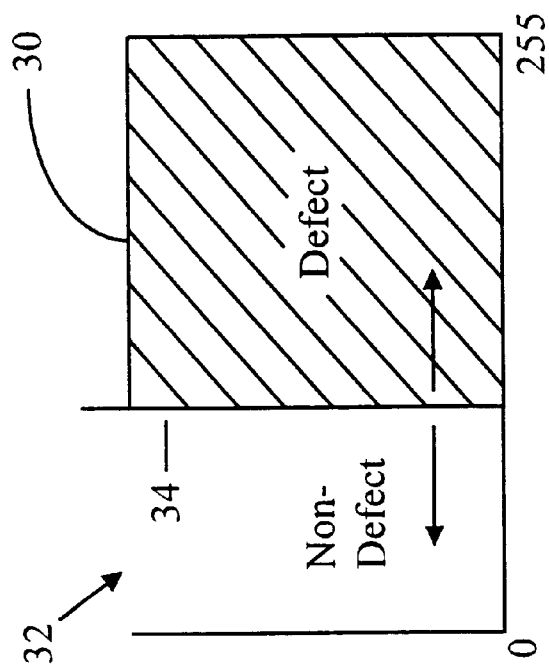
FIG. 2a is a graph of the results of a prior art brightfield inspection wherein a threshold level is determined and all signals having a signal above that value are classified as defects.

FIGS. 2a and 2b illustrate the defect decision technique of the prior art. Namely, the establishment of a linear decision boundary (34 or 40) separately in each of the brightfield data and the darkfield data with everything represented by signals having values (32 or 38) below that boundary being accepted as a non-defect areas on wafer 14, while the areas on wafer 14 that correspond with the signals having values (30 or 36) above that boundary being identified as defect regions. As will be seen from the discussion with respect to the present invention, the defect/non-defect boundary in reality is not linear which the prior art defect detection machines assume it to be.

Figure 3:
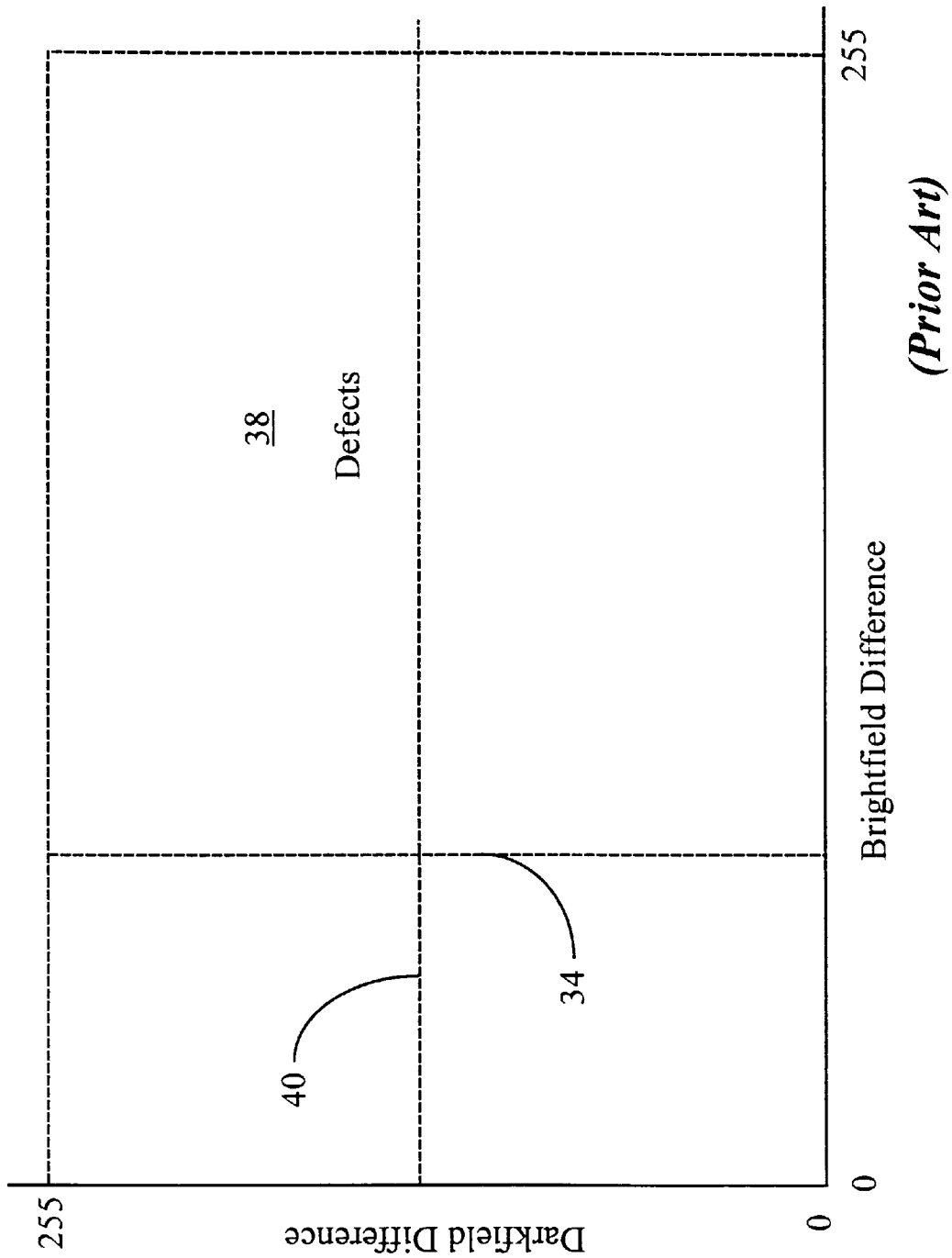
FIG. 3 is a plot of the brightfield difference versus the darkfield difference signals of the prior art with defects being associated with those regions of the wafer being tested that have a brightfield and darkfield difference signal that exceeds both thresholds.

Referring next to FIG. 3, there is shown a plot of the brightfield difference versus the darkfield difference with the individually determined brightfield and darkfield thresholds 34 and 40, respectively, indicated. Thus, given the prior art if it were decided to use both brightfield and darkfield data to determine more accurately which are the actual defects, which is not done, then only those regions associated with both brightfield and darkfield difference signals that exceed the respective brightfield or darkfield threshold levels would be identified as defects (i.e., region 38 in FIG. 3).

Figure 2C:
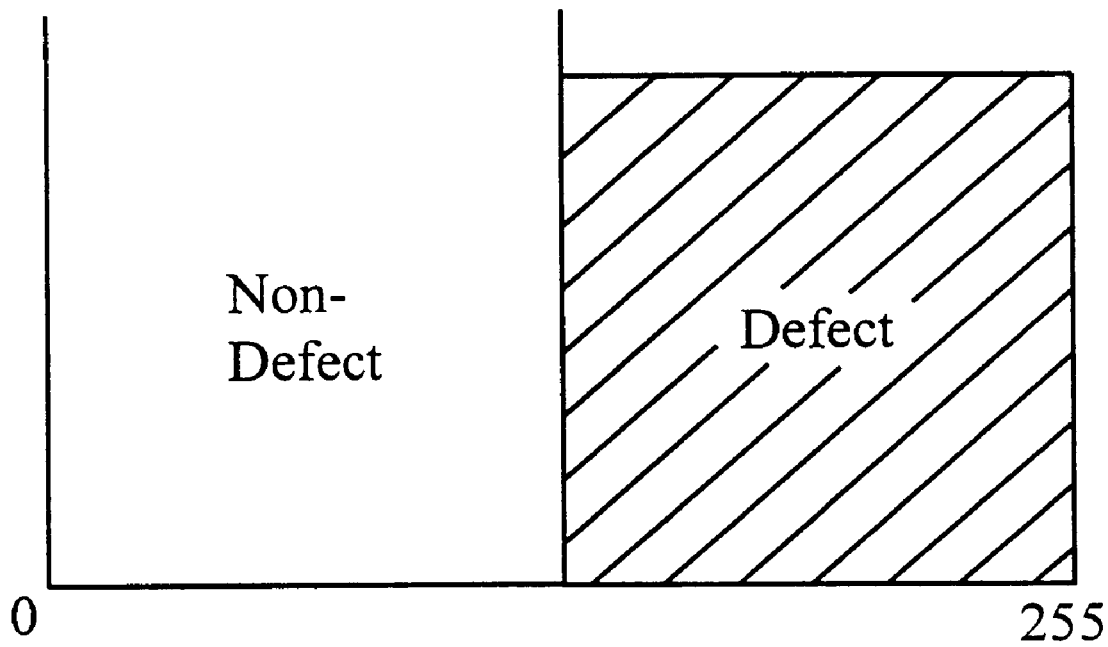
FIG. 2c is a graph of the results of a prior art full-sky inspection wherein a threshold level is determined and all signals having a signal above that value are classified as defects.

In the few machines that are available that simultaneously use both brightfield and darkfield illumination, they do so to provide what has come to be known as full-sky illumination (e.g., Yasuhiko Hara, Satoru Fushimi, Yoshimasa Ooshima and Hitooshi Kubota, "Automating Inspection of Aluminum Circuit Pattern of LSI Wafers", *Electronics and Communications in Japan, Part* 2, Vol. 70, No.3, 1987). In such a system, wafer 14 is simultaneously illuminated by both brightfield and darkfield illumination 10 and 12, probably from a single illumination source, and employs a single sensor 16 and single processing path 18-24 that results in a single output as shown in FIG. 2c from the full-sky illumination, not the two responses from the two separate runs as just discussed above. Here the threshold is also an unrealistic linear threshold.

Figure 4:
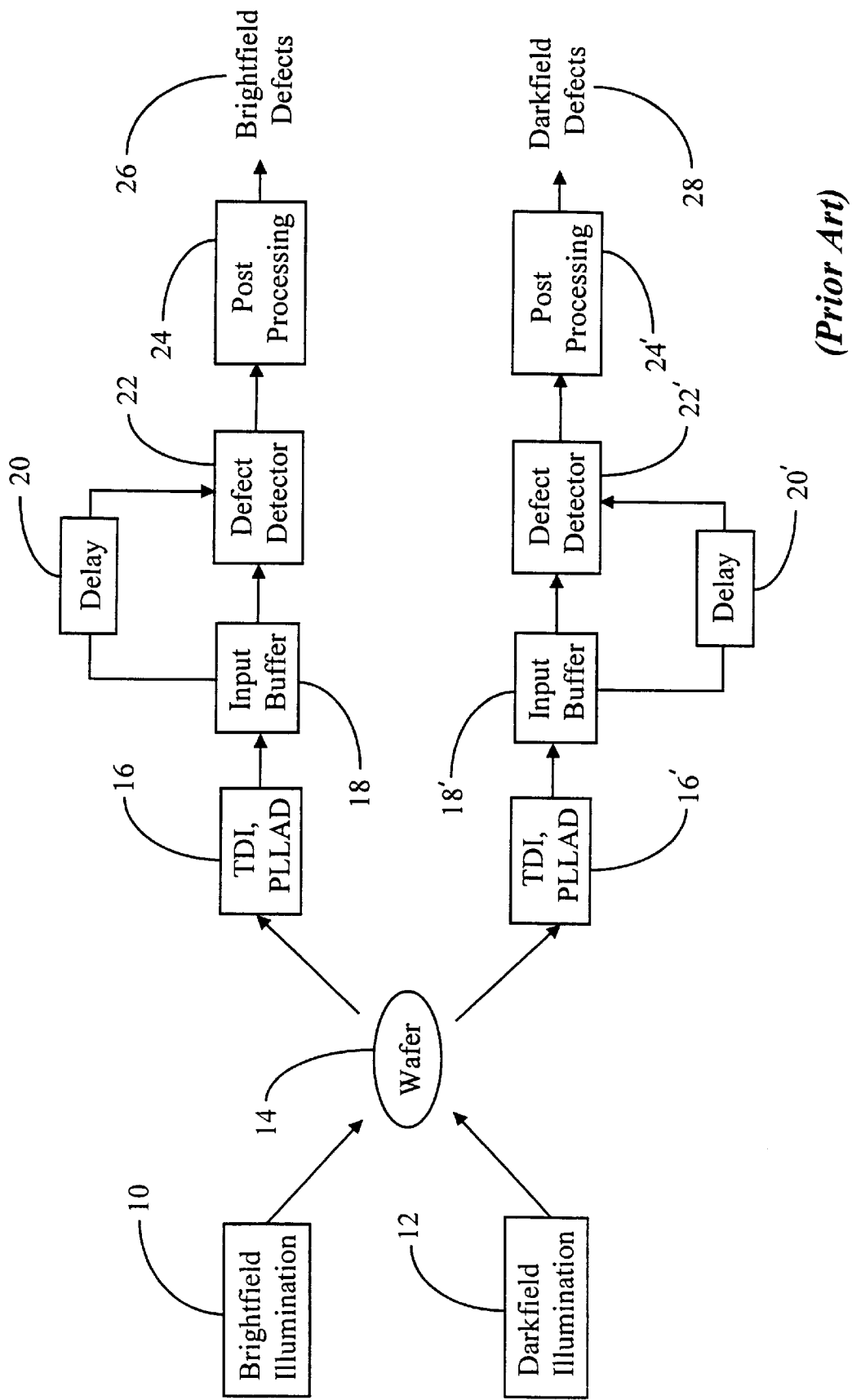
FIG. 4 is a block diagram of a prior art inspection system that has been modified to perform brightfield and darkfield inspection of a wafer in two separate signal processing channels.

FIG. 4 illustrates a second modification of the defect detection instruments of the prior art to perform both brightfield and darkfield defect detection concurrently. This can be accomplished by including two data processing channels, one for brightfield detection and a second one for darkfield detection. In such an instrument there would be either a single light source or dual brightfield and darkfield light sources that are used either sequentially, or together in a full-sky mode, that provides both brightfield and darkfield illumination to wafer 14. The difference between the configuration shown here and that in FIG. 1, is that the single processing channel of FIG. 1 has been duplicated so that both the brightfield and the darkfield operations can be performed simultaneously or separately in the same way that each run was performed in the configuration of FIG. 1 with each channel being substantially the same as the other. This then results in the simultaneous and separate generation of brightfield defect list 26 and darkfield defect list 28, independent of each other.

A system as shown in FIG. 4 has an advantage over that of FIG. 1, if the processes of each path is synchronized with the other so that they each proceed at the speed of the slowest, in that the brightfield and darkfield inspections are done in a single scan resulting in the two defect lists, or maps, being in alignment, one with the other since the data is developed in parallel and concurrently. However, as with the prior art system of FIG. 1, the system of FIG. 4 results in independent brightfield and darkfield lists (26 and 28) each with an independently determined defect threshold that linearly determines what is a defect and what is not a defect. Thus, what is shown in, and the discussion which accompanies each of FIGS. 2a, 2b and 3, apply equally to the system of FIG. 4.

Figure 5A:
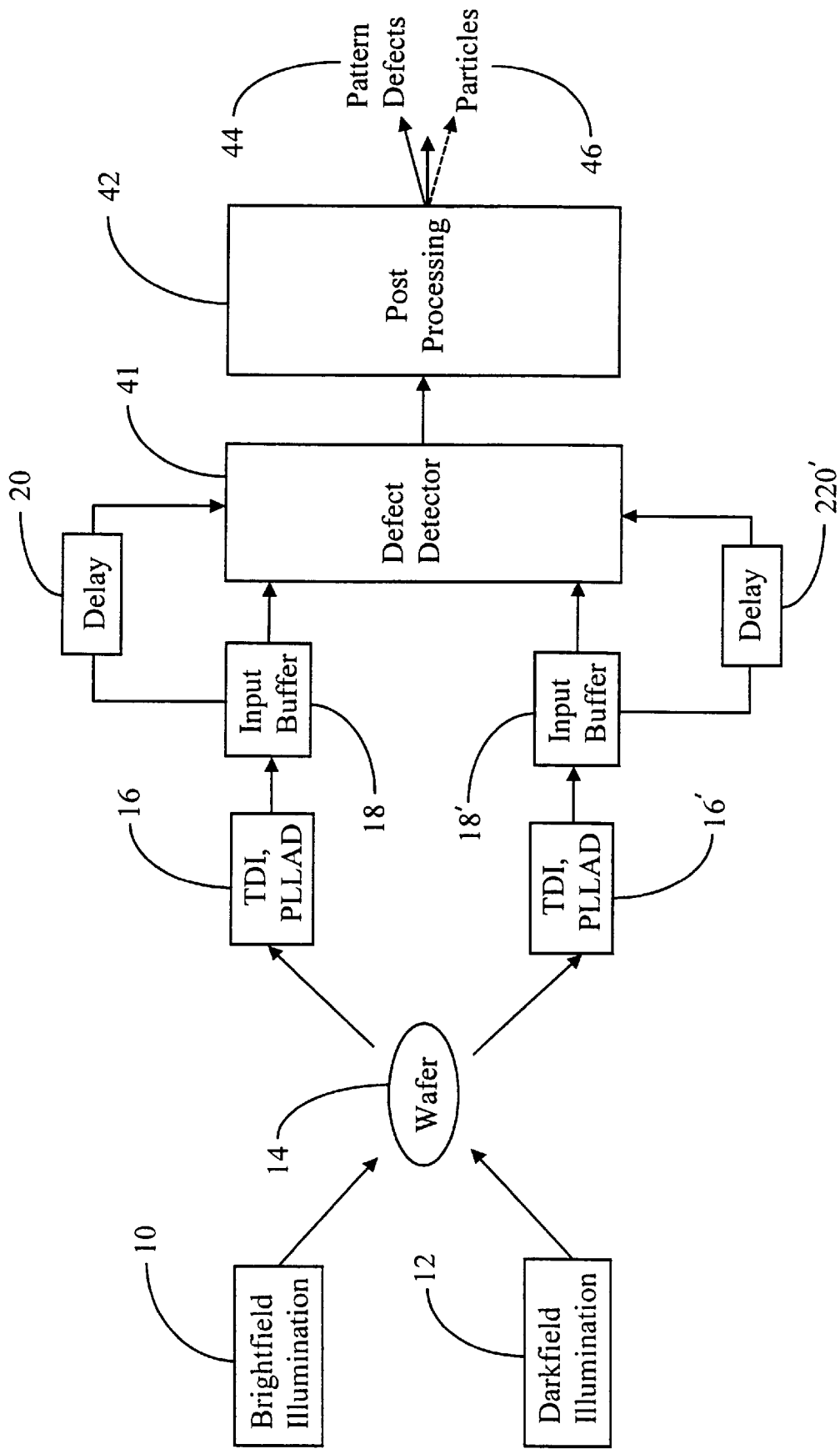
FIG. 5a is a block diagram of the inspection system of the present invention that performs brightfield and darkfield inspection of a wafer in the same processing channel.

Turning now to the present invention. FIG. 5a is a block diagram representation of the present invention. The left side is similar to the left side of the prior art diagram of FIG. 4 with the exception that the brightfield and darkfield images of wafer 14 are individually captured by brightfield and darkfield sensors 16 and 16', respectively, with the signals representing those images from sensors 16 and 16' being applied individually to brightfield and darkfield buffers 18 and 18', respectively, with individual delay lines 20 and 20' therefrom. That is where the similarity to the extension of the prior art of FIG. 4 ends.

From buffers 18 and 18', and delays 20 and 20', the signals therefrom, those signals being representative of both the brightfield and the darkfield images, are applied to a single defect detector 41 (shown in and discussed in more detail relative to FIG. 5b) where the information from both images is utilized to determine the locations of the defects on wafer 14. The overall, combined, unilaterally determined defect list from defect detector 41 is then operated on by post processor 42 to identify the pattern defects 44 and particles 46. Post processor 41 can be based on a high performance general purpose Motorola 68040 CPU based VME (Virtual Machine Environment) bus processing boards or a high performance post processor board that is similar to the post processor used in KLA Instruments Model 2131.

It is known that semiconductor wafers often include surface features such as contrast variations, grain and grain clusters, as well as process variations that may be a chemical smear, each of which do not impact the performance of a die produced on such a wafer. Each of these surface features also have a typical range of brightfield and darkfield image values associated with them. Additionally, as with any imaging system, there is some noise associated with the operation of the detection system and that noise causes variations in the brightfield and darkfield difference signals at the low end of each.

Figure 6:
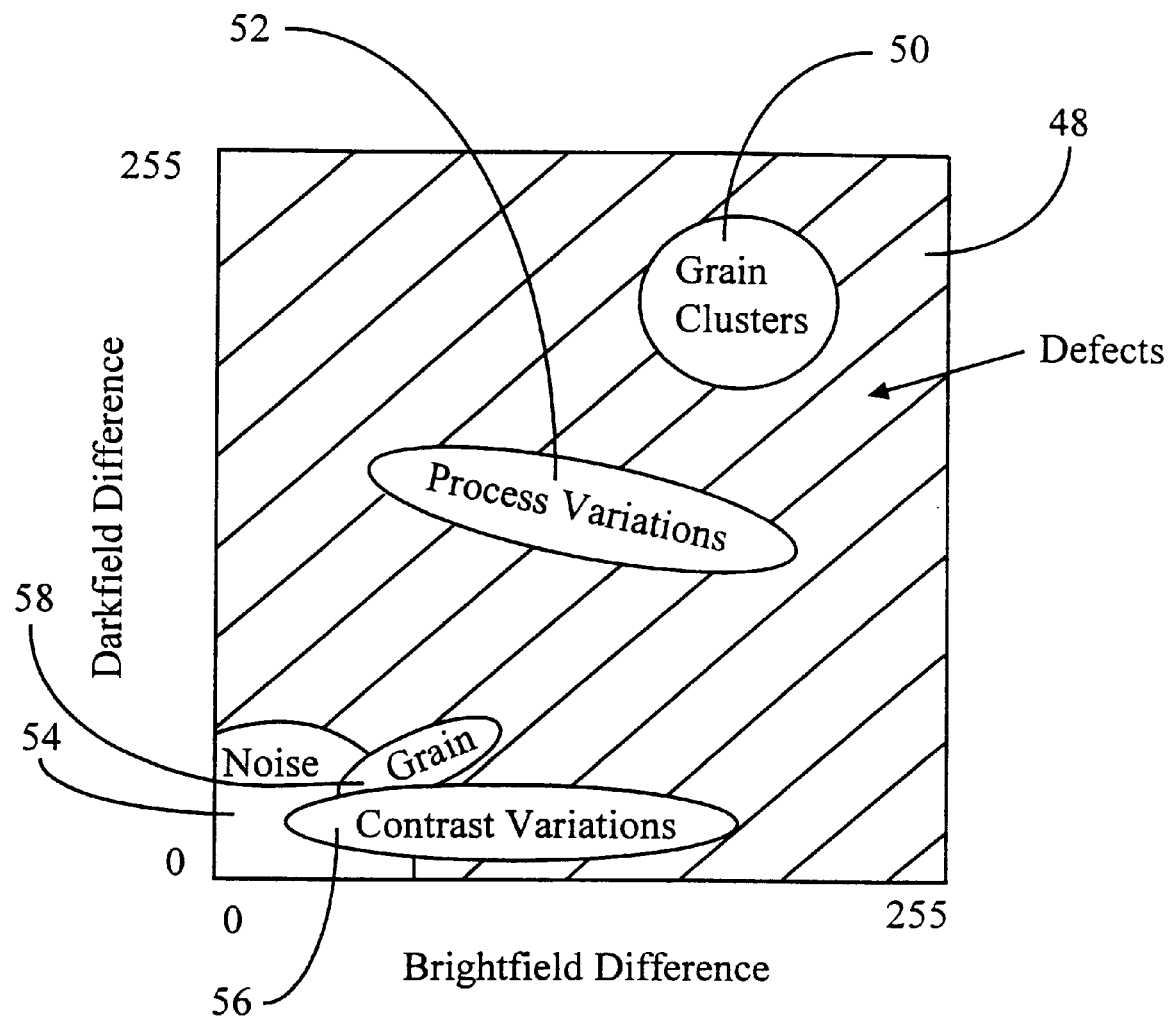
FIG. 6 is a plot of the brightfield difference versus the darkfield difference of the present invention with defects being associated with those regions that have not been programmed into the post processor as being those regions that are not of interest.

Thus, if the typical range of brightfield and darkfield difference values of those surface features and system noise are plotted against each other, then they generally appear as in FIG. 6. Here it can be seen that system noise 54, surface contrast variations 56 and grain 58 appear for low values of both brightfield and darkfield difference values, process variations are over about 75% of the range for brightfield and mid-range for darkfield difference values, and grain clusters appear in the higher values of both brightfield and darkfield difference values. Ideally the best system would be one that can exclude these predictable variations without identifying them as defects, and to be able to thus identify all other responses 48 as defects.

Figure 5B:
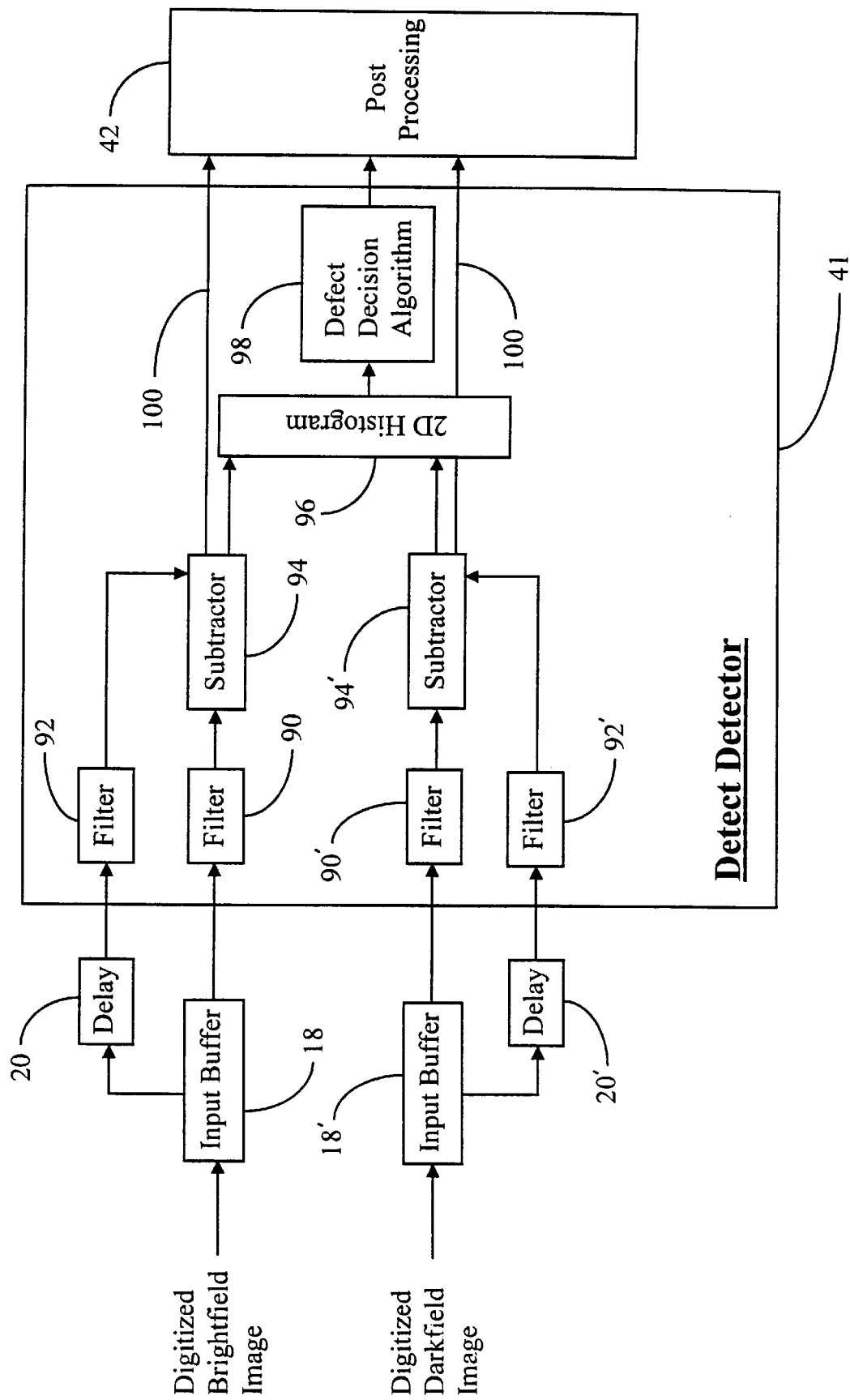

FIG. 5b is a partial block diagram of the circuit shown in FIG. 5a with added detail of defect detector 41. In this simplified block diagram of defect detector 41, the input signals are received from input buffers 18 and 18', and delays 20 and 20', by filters 90, 90', 92 and 92', respectively. Each of filters 90, 90', 92 and 92' are used to pre-process the image data and can be implemented as 3×3 or 5×5 pixel digital filters that are similar to those used for the same purpose in KLA Instruments Model 2131. The pre-processed images from filters 90 and 92, and 90' and 92', are applied to subtractor 94 and 94', respectively, where the brightfield and darkfield images are compared with the delayed version with which a comparison is performed. Where, for die-to-die comparison, the delay is typically one die wide, and for cell-to-cell comparison, the delay is typically one cell wide, with the same delay being used in both the brightfield and darkfield paths. Thus, the output information from subtractors 94 and 94' is, respectively, the brightfield and darkfield defect information from wafer 14. That information, in turn, is applied to both a two dimensional histogram circuit 96 and post processor 42. Thus, that information applied directly to post processor 42 provides the axis values for FIG. 6, while two dimensional histogram circuit 96 forms the two dimension histogram of the defect data with brightfield difference on one axis and darkfield difference on the other axis in FIG. 6. That histogram information is then applied to a defect decision algorithm 98 to determine the boundaries of the known types of surface and other variations (e.g., system noise, grain, contrast variation, process variations, and grain clusters, and any others that are known to result routinely from a particular process that do not present an operational problem on the finished item).

Figure 7:
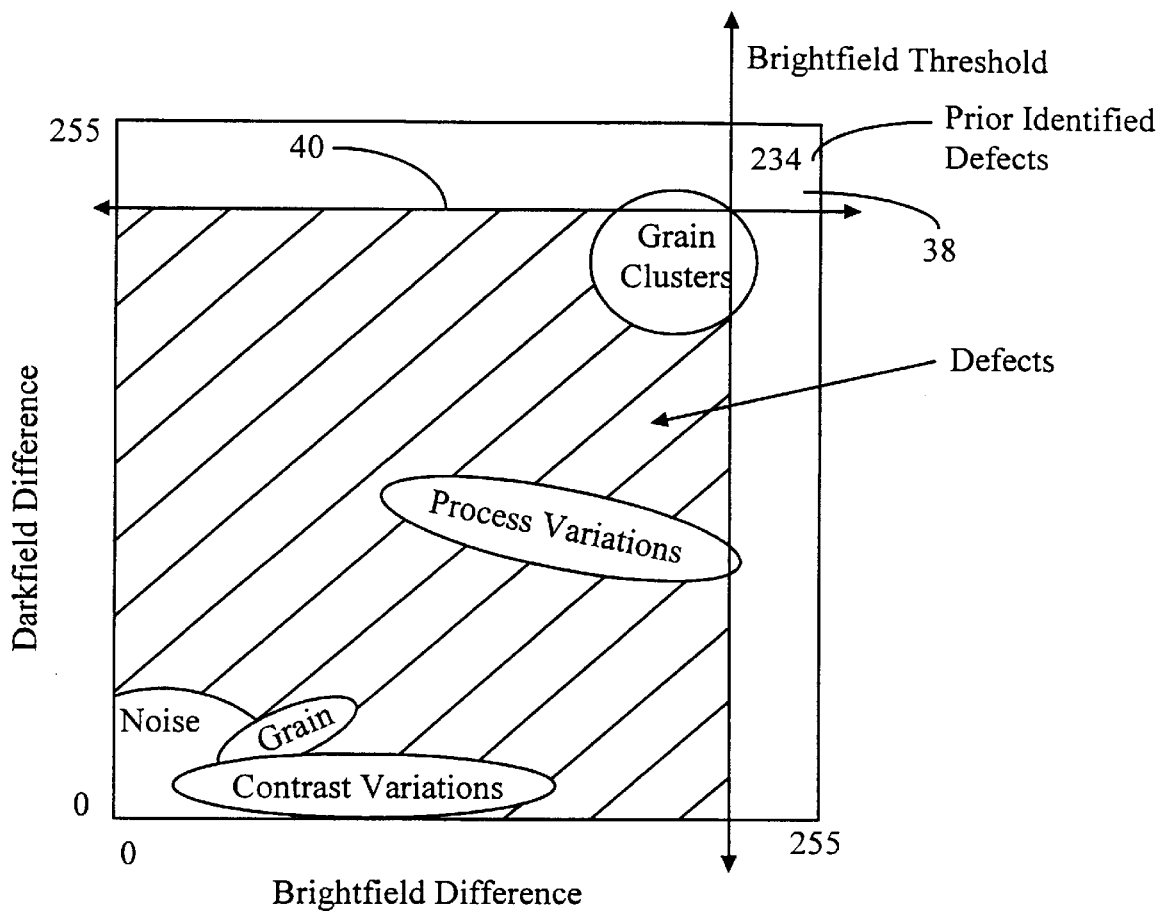
FIG. 7 is a plot of the combination of the plots of FIGS. 3 and 6 to illustrate where the brightfield and darkfield thresholds in the prior art would have to be placed to avoid all of the regions of this plot that are not of interest.

FIG. 7 illustrates what would have to be done with the prior art approach to avoid the identification of any of those predictable and non-injurious responses as defects. Namely, the linearly determined brightfield and darkfield thresholds 34 and 40 would have to be selected so that each is above the values of these expected responses. Thus, region 38, the combined defect region, would be very small resulting in a substantially useless approach to the problem.

Referring again to FIG. 6, on the other hand, since the present invention processes the individually developed brightfield and darkfield imaging data simultaneously, defect detector 41 is programmed to define complex threshold functions for both the brightfield and darkfield difference values to exclude only those regions of expected variation and thus be able to look at the remainder of all of the difference values 48 for both brightfield and darkfield as illustrated in FIG. 6 as all of the regions not identified by the expected causality. Stated in other words, the present invention can consider all values, 0–255 for each of the two difference signals that are not contained in regions 50, 52, 54, 56 and 58 of FIG. 6 as representing defects including low values from both the brightfield and the darkfield differences.

Figure 8:
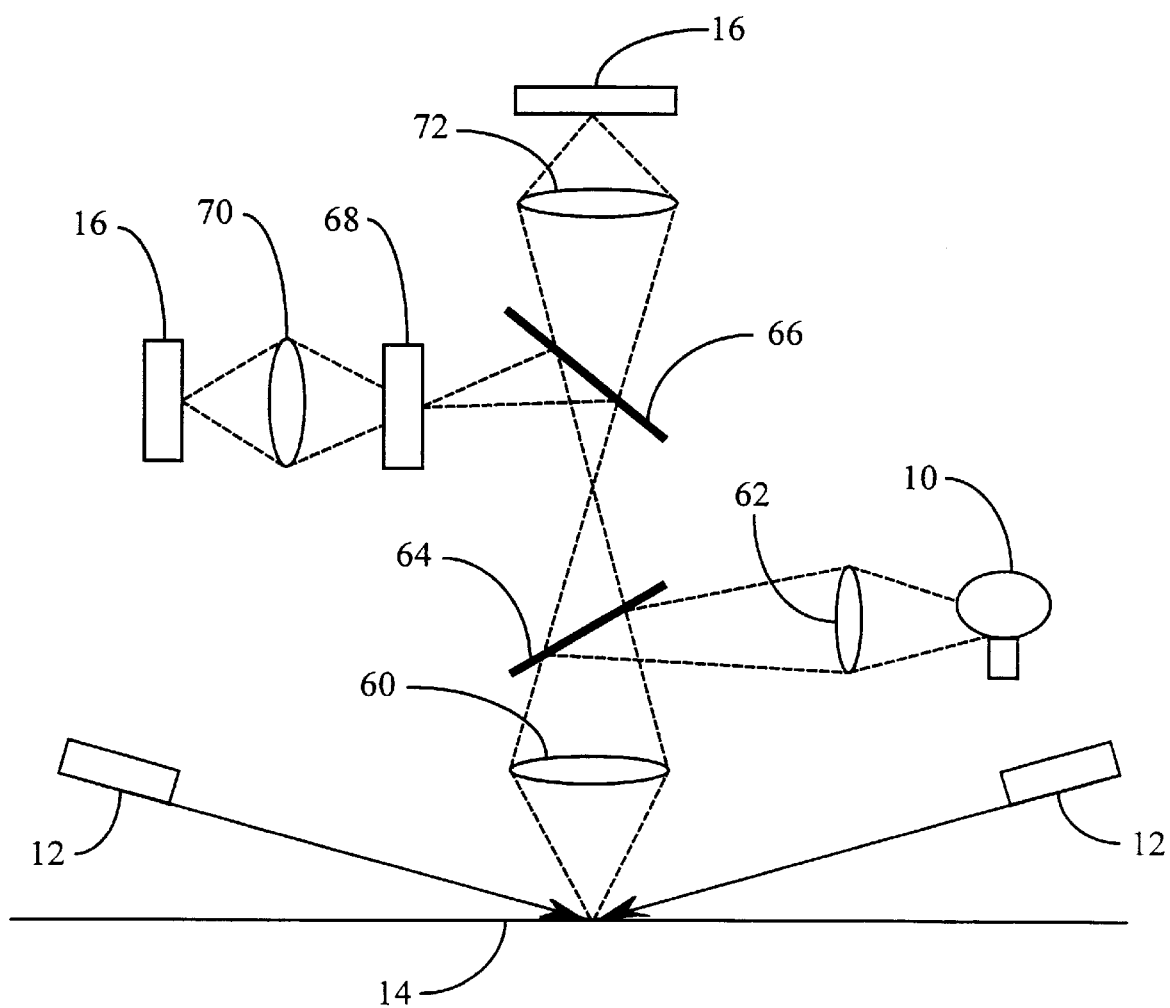
FIG. 8 is a simplified schematic diagram of a first embodiment of the present invention that uses separate brightfield and darkfield illumination sources.

One physical optical embodiment of the present invention is shown in the simplified schematic diagram of FIG. 8. Here, wafer 14 is illuminated directly by a darkfield illumination source 12 (e.g., a laser), and a brightfield illumination source 10 (e.g., a mercury arc lamp) via lenses 60 and 62 and beamsplitter 64.

The combined brightfield and darkfield image reflected by wafer 14 travels upward through condensing lens 60, through beamsplitter 64 to beamsplitter 66. At beamsplitter 66 the brightfield image continues upward to condensing lens 72 from which it is projected onto brightfield sensor 16. The darkfield image, on the other hand, is reflected by a dichroic coating on beamsplitter 66 given the frequency difference in the brightfield and darkfield light sources to spatial filter 68, to relay lens 70 and onto darkfield image sensor 16'.

In the embodiment described here, the darkfield illumination is provided by a laser with spatial filter 68 corresponding to the Fourier transform plane of the image of wafer 14. In such an embodiment, spatial filter 68 is constructed to selectively black out non-defective, regular patterns, to further improve defect detection.

By using two separate light sources, brightfield illumination from a mercury arc lamp via beamsplitter 64 and darkfield illumination from a laser, with the ability to perform spatial filtering, as well as the laser brightness/power properties, the light loss is limited to a few percent when the brightfield and darkfield information is separated.

The use of a narrow band laser source for darkfield illumination makes it possible to select either a longer wavelength laser, such as HeNe at 633 nm, or laser diodes in the range of about 630 nm to 830 nm, and separate the darkfield response from the overall response with the dichroic coating on beamsplitter 66, or any laser could be used with the darkfield response separated out with a laser line interference filter, such as a Model 52720 from ORIEL. In the latter case with the narrow band spectral filter, the brightfield system can use a mercury line filter, such as a Model 56460 from ORIEL. Additionally, a special, custom design laser narrow band notch filter can also be obtained from ORIEL. Thus the spatial filtering is applied only to the darkfield path, so the brightfield path will not be affected in image quality.

The use of narrow band light sources (e.g., lasers for darkfield) is necessary for spatial filtering. The narrow band nature of a laser also allows easier separation of brightfield and darkfield signals by a filter or beamsplitter.

Spatial filter 68 can by made by exposing a piece of a photographic negative in place as in FIG. 8, then remove and develop that negative, and then reinsert the developed film sheet back at location 68. Alternatively, spatial filter 86 can be implemented with an electrically addressed SLM (Spatial Light Modulator), such as an LCD (Liquid Crystal Display), from Hughes Research Lab.

The preferred approach for the separation of the darkfield image information from the overall image response, given the choice of optical components presently available, is the use of a beamsplitter 66 with a dichroic coating and a spatial filter 68 since it produces better control of the dynamic range/sensitivity of the system and the ability of the system to perform the simultaneous inspection with the brightfield image information. However, given advances in optical technology, the dichroic beamsplitter approach, or another approach not currently known, might prove more effective in the future while obtaining the same result.

Figure 9:
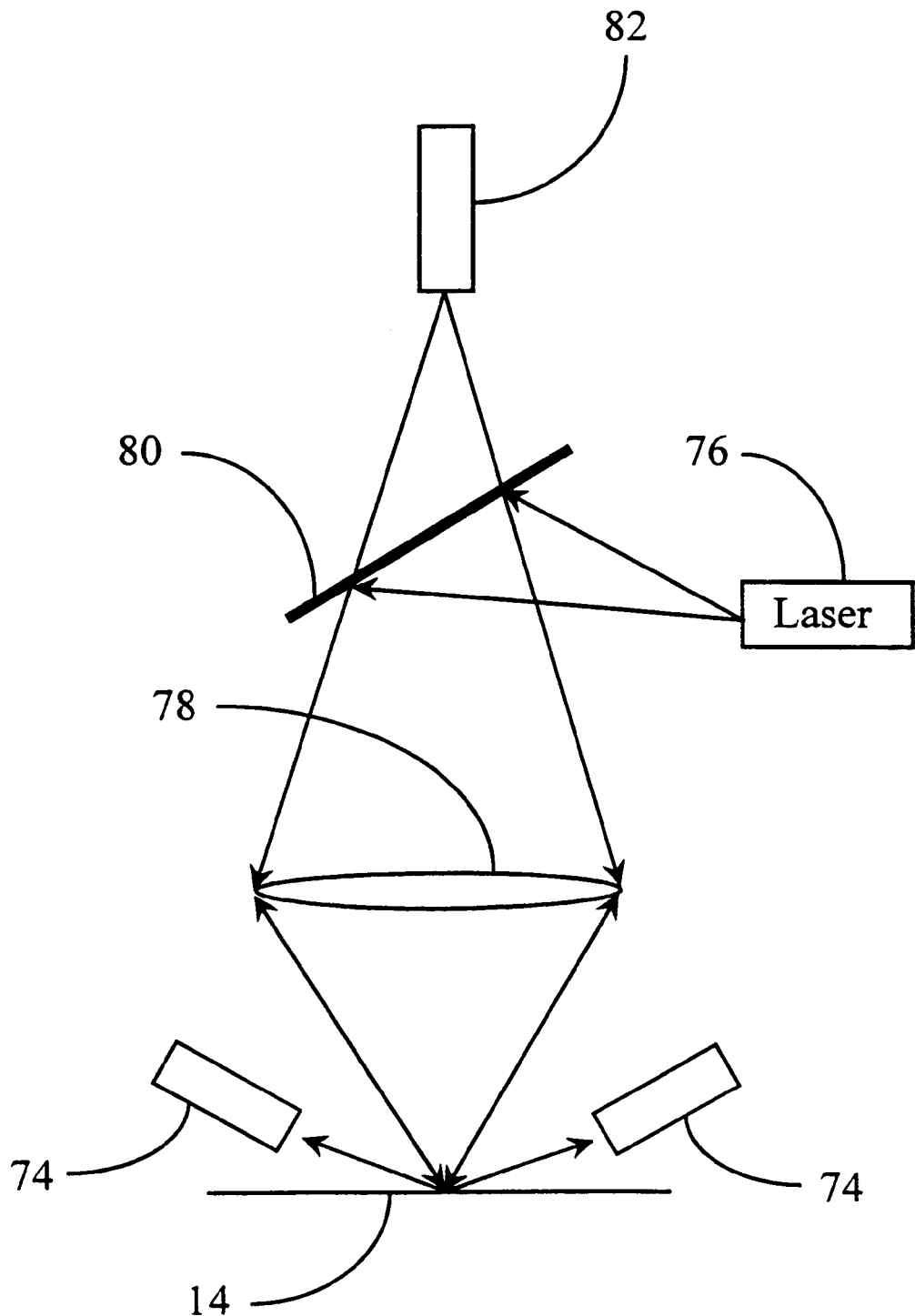
FIG. 9 is a simplified schematic diagram of a second embodiment of the present invention that uses a single illumination source for both brightfield and darkfield illumination.

FIG. 9 is a schematic representation of a second embodiment of the present invention. In this embodiment a single laser 76 provides both brightfield and darkfield illumination of wafer 14 via beamsplitter 80 that reflects the light downward to condenser lens 78 and onto wafer 14. Simultaneous brightfield and darkfield imaging is performed in this embodiment with darkfield detectors 74 at a low angle to wafer 14 and brightfield sensor 82 directly above wafer 14 receiving that information from wafer 14 via condenser lens 78 and through beamsplitter 80. To optimize defect detection using this embodiment, the output signals from brightfield detector 82 and darkfield detectors 74 are processed simultaneously to detect the defects of interest.

The approaches described here, using broadband brightfield and spatial filtered darkfield images in die-to-die comparison, overcomes all the limitations of existing machines. The existence of the brightfield image allows for a very accurate alignment of images from two comparison dies. By pre-aligning the darkfield and brightfield sensors so they both image the exact same area, the alignment offsets only need to be measured in the brightfield channel and then applied to both channels. This is possible since the offset between the brightfield and darkfield sensors is fixed, having been adjusted and calibrated at the time of machine manufacture, thus such offset remains fixed in machine operation with that offset remaining known. Thus the high speed alignment offset measurement electronics need not be duplicated for the darkfield channel. Using the alignment information from the brightfield images, the darkfield channel can also achieve a very accurate die-to-die alignment so detection of small particles is no longer limited by the residual alignment error. As stated above, the use of spatial filtering in the darkfield processing is currently preferred to filter out most of the repeating patterns and straight line segments, equalizing the dynamic range so small particles can be detected in both dense and sparse areas in one inspection.

In addition, the simultaneous consideration of darkfield and brightfield images offers significantly more information. For example, because brightfield imaging permits the detection of both pattern and particle defects and darkfield imaging permits the detection only of particles, the difference of the two results is pattern defects only. This ability to separate out particles from pattern defects automatically in real time is an unique capability of the technique of the present invention, which is of great value in wafer inspection systems. For this particular application, since darkfield imaging is more sensitive to particles than brightfield imaging, the darkfield imaging sensitivity can be slightly reduced to match that of brightfield imaging so that the defects detected by both channels are particles and defects detected only by brightfield imaging are pattern defects. Another example is inspection of metal interconnect layers of semiconductor wafers. One would also expect that by combining the results from darkfield and brightfield imaging, nuisance defects from metal grain can be better separated from real defects.

The brightfield and darkfield images, and corresponding delayed images, could be collected and stored individually, and then fed, in alignment, into, defect detector 41 as in FIG. 5*a*. In order to perform the detection in this way a dynamic RAM that is Gigabytes in size would be necessary to store the data and the data would have to be read out of that RAM in registration with each other as is done in the real time process of FIG. 5*a* as discussed above. While this is feasible and may become attractive in the future, given today's technology the preferred approach is to inspect the wafer in both brightfield and darkfield in real time for faster time to results with this approach being more cost effective in today's market.

In whatever implementation that is used, the brightfield and darkfield images from the same point on wafer 14 are observed by two different detectors. It is very important to know from the same location on wafer 14, what the relationship of the brightfield and darkfield images are (e.g., where the darkfield signal is strong and the brightfield signal is weak). Simply adding the two signals together does not yield the same result—that differentiation is cancelled out which reduces the ability to detect defects.

What the present invention provides is different illumination at different angles, which is separated out to yield a full characteristic of what is actually occurring on wafer 14. To perform this operation, it is necessary that the two sensors be aligned and registered with each other. Thus, since that alignment and registration are expensive and increase the complexity of the defect detection system, the advantages that have been recognized by the present invention were not known since that has not been done in the prior art.

Further, while the discussion up to this point has been limited to using single frequency brightfield and darkfield illumination for defect detection, the technique of the present invention can naturally be extended to include more channels of information (e.g., multiple frequencies of both brightfield and darkfield illumination). The key to this extension is the same as has been discussed for the two channels of information discussed above, namely, each would have to be applied to the same region of wafer 14 and individually detected with a separate detector, followed by a combination of the detected results as has been discussed with relation to FIG. 6 for just the two.

If there are more than two channels of information, FIG. 6 becomes multi-dimensional. While it is not possible to illustrate more than three dimensions on paper, computers and numerical methods are readily available to deal with multi-dimensional information.

Figure 10:
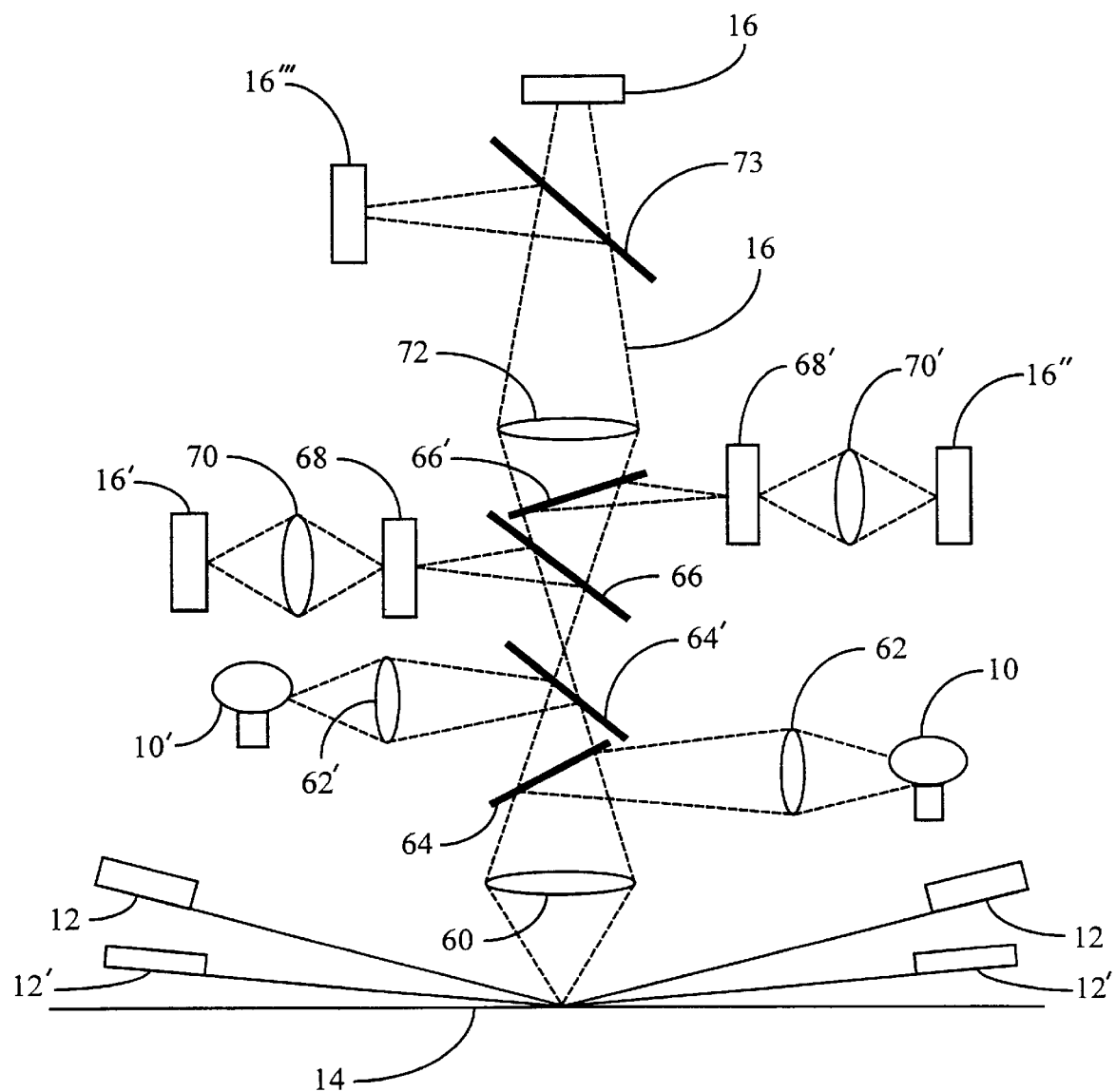
FIG. 10 is a simplified schematic diagram of a third embodiment of the present invention that is similar to that of FIG. 8 with two darkfield illumination sources, two brightfield illumination sources, and two darkfield detectors and two brightfield detectors.

FIG. 10 is FIG. 8 modified to handle multiple brightfield and darkfield images, namely two of each. Rather than repeat the entire description of FIG. 8, let it be understood that all of the elements of FIG. 8 remain here and function in the same way as in FIG. 8. For the second darkfield channel, lasers 12' that operate at a different frequency than laser 12 have been added to illuminate the same location on the surface of specimen 14. To provide the second brightfield illumination to specimen 14, light source 10' of a different frequency than light source 10, lens 62' and beamsplitter 64' have-been provided to also direct brightfield illumination to again the same location on specimen 14. In the reflective mode also the operation is similar to that of FIG. 8 with the addition of beamsplitter 66' with a dichroic film thereon to reflect light of the frequency from the second lasers 12' to spatial filter 68', lens 70' and detector 16'''. Further, beamsplitter 73 with a dichroic film thereon to reflect light of the frequency from one of the brightfield illumination sources 10 and 10' to detector 16''', with the light passing through beamsplitter 73 being light of the frequency of the other brightfield illumination since the other light has been subtracted from the direct reflected beam by beamsplitters 66, 66' and 73.

It should be understood that the embodiment of FIG. 10 is just one modification of the embodiment that is shown in FIG. 8. To particularly identify specific defects from other defects, there is any number of combinations of the various types of components that may need to be employed. While those specific embodiments may be different from that discussed here, the concept remains the same, the use of multiple channels of information for making defect decisions, unlike the prior art which relies on a single channel of information, namely either darkfield or brightfield, not both.

Alternately, multiple passes with different wavelengths of brightfield and darkfield light in each pass could be used, for example.

Figure 11:
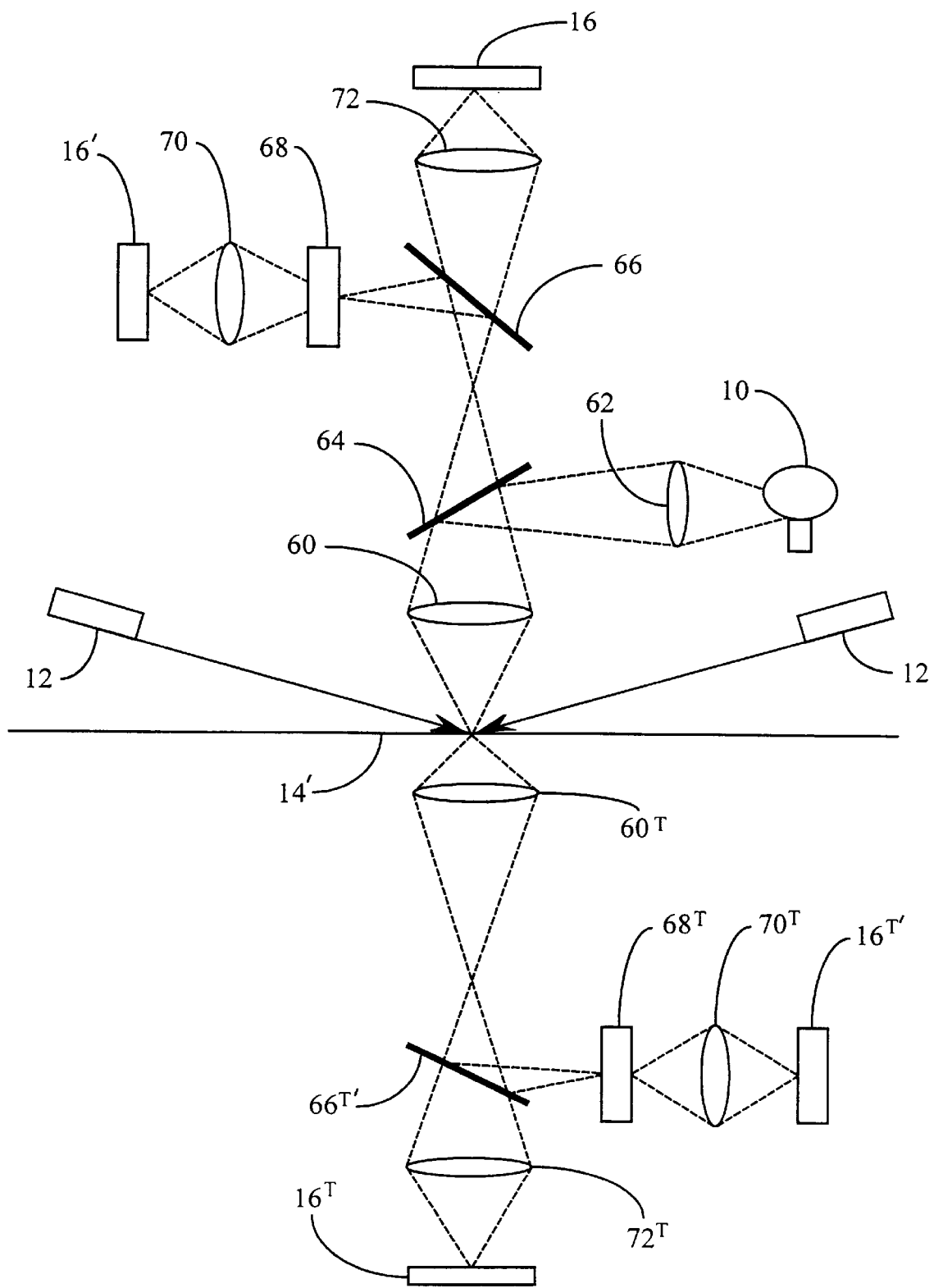
FIG. 11 is a simplified schematic diagram of a fourth embodiment of the present invention that uses separate brightfield and darkfield illumination sources for inspecting a specimen that is transmissive.

Additionally, the technique discussed here for wafers could also be extended to transmissive materials that one might want to detect defects on or in. In such an application, transmitted brightfield and darkfield light could also be detected and integrated with the reflected brightfield and darkfield signals to determine the locations of various defects. FIG. 11 illustrates a simplified embodiment to accomplish that. The difference between what is shown here and in FIG. 8, is that only similar light detection components are reproduced beneath specimen 14'.

The combined transmitted brightfield and darkfield image information travels downward from the bottom surface of specimen 14' through condensing lens $60^T$ to beamsplitter $66^T$. At beamsplitter $66^T$ the brightfield image continues downward to condensing lens $72^T$ from which it is projected onto transmitted brightfield sensor $16^T$. The transmitted darkfield image, on the other hand, is reflected by a dichroic coating on beamsplitter $66^T$ given the frequency difference in the brightfield and darkfield light sources to spatial filter $68^T$, to relay lens $70^T$ and onto sensor darkfield image $16^{T'}$.

The concepts of the present invention have been discussed above for the specific case of brightfield and darkfield illumination and independent detection of the brightfield and darkfield responses from the specimen. In the general case the present invention includes several elements:

a) at least one probe to produce at least two independent optical responses from the same area of the same die of the specimen being inspected and if more than one probe is used all of the probes are aligned to direct their energy to the same area of the same die of the specimen;

b) individual detection of each of the optical responses and comparison of each response with a similar response from the same area of another die of the specimen with the responses from the two die being compared to create a difference signal for that optical response; and c) processing the multiple response difference signals together to unilaterally determine a first pattern defect list.

This generalized process can also be extended as has the brightfield-darkfield example given above by post processing the first pattern defect list to identify known nonperformance degrading surface features and eliminating them from the final pattern defect list.

In the specific discussion of the figures above one or more probes where discussed to produce two or more optical responses. In FIG. 9 there is a single probe, laser 76, that is providing both brightfield and darkfield illumination of the specimen, wafer 14, and there are two independent detectors, darkfield detectors 74 and brightfield detector 82 for two channels of information. In FIG. 8 there are two probes, laser 12 that is providing darkfield illumination of the specimen, wafer 14, and lamp 10 that is providing brightfield illumination of the specimen; and there are two independent detectors 16 and 16' for reflections of the brightfield and darkfield illuminations respectively for two channels of information. FIG. 10 is an extension of the system of FIG. 8 with second darkfield and brightfield sources being added thus making for four probes, as well as an additional one of each a darkfield detector and a brightfield detector making for four channels of information. Also, FIG. 11 is similar to FIG. 8 with two probes, brightfield and darkfield illumination, and the addition of the detection of transmitted brightfield and darkfield radiation for a total of four channels of information, reflected and transmitted brightfield and reflected and transmitted darkfield.

In each of the examples given above, there has been no frequency or phase shift between the illumination emitted by the probe and the detector, other than for sorting between the brightfield and darkfield signals. Fluorescence is a well known response by some materials when exposed to radiation within a particular frequency band. When a material fluoresces the secondary radiation from that material is at a lower frequency (higher wavelength) than the frequency (wavelength) of the inducing, or probe, illumination. With some material, to detect potential defects it may be advantageous to be able to monitor the frequency shift produced by that fluorescence. Since the frequency at which each material fluoresces is well known, dichroic coatings on beamsplitters and detectors that are sensitive to those frequencies can be included in the imaging path to detect that effect together with others that are considered of value.

Similarly, when there is a difference in the optical path from the probe to different portions of the surface of the specimen (e.g., a height variation, perhaps in the form of a step on the surface of the specimen, or different regions with different indices of refraction) the reflected illumination will be phase shifted with respect to the probe emitted illumination. Some types of defects it would prove advantageous to have phase information as one channel of information to the defect detector. Interferometers are readily available to detect this phase shift, and can also detect contrast variations on the surface of the specimen. There are a variety of interferometers available including Mach-Zehnder, Mirau, Jamin-Lebedeff, as well as beam-shearing interferometers to serve this purpose. Additionally, the magnitude of the gradient of the change in phase can be monitored with a differential, or Nomarski, interference contrast microscope.

Also related to phase information is polarization changes that may occur as a result of a feature of the specimen, that also could provide a channel of information. For instance, if the specimen is spatially varying in birefringence, transmitted probe light will reveal this information. Similarly, if the specimen has polarization-selective reflection or scattering properties, reflected probe light will reveal this information. The polarization shift of the probe light can also be detected with readily available detectors and provide an additional channel of information for the inspection process of a specimen from either above or below the specimen depending on the construction of the specimen and the angle of illumination.

Confocal illumination is another type of probe that might be considered to make the detection of the topography of the specimen another channel of information.

Yet another technique that can be used with most of the probe variations that have been mentioned, as well as others that have not, and may not have yet been discovered, is the inclusion of temporal information (e.g., pulsing the illumination on/off with a selected pattern) in the probe illuminations. That temporal signal then could be used in the detection step to sort, or demultiplex, the responses to that signal from the others present to simplify detection. Any time shift, or time delay, in that temporal signal could also be used in the detection step to determine topographical features that may be present on or in the specimen.

There are also several available cameras that have multiple sensors in the same package. An RGB (red-green-blue) camera is such a camera that utilizes three CCDs in the same envelope. The use of such a camera automatically yields alignment of all three sensors by the single alignment step of each CCD. Here each is a separate sensor with individual signal processing.

In each of the embodiments of the present invention it is necessary that each of the probes be aligned to direct their energy to the same location on the specimen, and, also, that each of the detectors be aligned to image the same size and location on the specimen.

While this invention has been described in several modes of operation and with exemplary routines and apparatus, it is contemplated that persons skilled in the art, upon reading the preceding descriptions and studying the drawings, will realize various alternative approaches to the implementation of the present invention. It is therefore intended that the following appended claims be interpreted as including all such alterations and modifications that fall within the true spirit and scope to the present invention and the appended claims.

What is claimed is:

1. An inspection system to inspect a first pattern on a specimen for defects a second pattern that is intended to be the same, said inspection system comprising:

a monochomatic probe sequentially directed to each point in said first pattern on said specimen;

a broadband probe sequentially directed to said each point in said first pattern on said specimen;

a monochomatic response detetor positioned to detect a first response from each point of said first pattern on said specimen generated by said monochomatic probe;

a broadband response detector positoned a second response from each point of said first pattern on said specimen generated by said broadband probe;

a first response comparator coupled to said monochomatic response detector to generate a first response difference signal by comparing the output from said monochromatic response detector for each point of said first pattern with a known first response to a monochromatic probe from each corresponding point on said second pattern to develop a first response difference signal;

a second response comparator coupled to said broadband response detector to generate a second response difference signal by comparing the output from said broadband response detector for each point of said first pattern with a known second response to a broadband probe from each corresponding point of said second pattern to develop a second response difference signal; and a difference map generator coupled to said first and second response comparators to receive said first and second response difference signals, respectively, to generate a difference map for said first pattern with values of said first and second difference signals the coordinates of said difference map for each point in said first pattern.

2. An inspection system as in claim 1 wherein said monochomatic probe emits a signal with a first frequency, said broadband probe emits a signal in a first band of frequencies, and said first frequency is outside said first band of frequencies.

3. An inspection system as in claim 1 wherein:

said monochomatic probe is directed to said first pattern at a low angle thereto;

said monochomatic response detector receives darkfield images from said first pattern on said specimen;

said broadband probe is directed to said first pattern in vicinity of perpendicular thereto; and said broadband response detector receives brightfield images from said first pattern on said specimen.

4. An inspection system as in claim 1 wherein:

said monochomatic probe is generated by a monochromatic light source;

said broadband probe is generated by a broadband light source; and said known first and second responses of said second pattern are darkfield and brightfield responses, respectfully.

5. An inspection system as in claim 1 further comprising a processor coupled to said difference map generator to receive said difference map of said first pattern to unilaterally determine defects for said first pattern from said difference map.

6. An inspection system as in claim 5 wherein said processor includes a subtractor to exclude regions of expected variation from said difference map of said first pattern to generate a defect map for said first pattern.

7. An inspection system to inspect a first pattern on a transmissive specimen for defects against a second pattern that is intended to be the same, wherein said specimen has a first surface and a second surface substantially parallel to said first surface, said inspection system comprising:

a monochomatic probe sequentially directed to each point in said first pattern on said first surface of said specimen;

a broadband probe sequentially directed to said each point in said first pattern on said first surface of said specimen;

a monochomatic reflected response detector positioned to detect a first reflected response from each point of said first pattern on said first surface of said specimen generated by said monochomatic probe;

a broadband reflected response detector positioned to detect a second reflected response from each point of said first pattern on said first surface of said specimen generated by said broadband probe;

a monochomatic transmitted response detector positioned to detect a first transmitted response from each point of said first pattern on said second surface of said specimen generated by said monochomatic probe;

a broadband transmitted response detector positioned to detect a second transmitted response from each point of said first pattern on said second surface of said specimen generated by said broadband probe;

a first reflected response comparator coupled to said monochomatic reflected response detector to generate a first reflected response difference signal by comparing the output from said monochomatic reflected response detector for each point of said first pattern with a known first reflected response from each corresponding point on said second pattern to develop a first reflected response difference signal;

a second reflected response comparator coupled to said broadband reflected response detector to generate a second reflected response difference signal by comparing the output from said broadband reflected response detector for each point of said first pattern with a known second reflected response from each corresponding point of said second pattern to develop a second reflected response difference signal;

a reflected difference map generator coupled to said first and second reflected response comparators to receive said first and second reflected response difference signals, respectively, to generate a reflected difference map for said first pattern with values of said first and second reflected difference signals the coordinates of said reflected difference map for each point in said first pattern;

a first transmitted response comparator coupled to said monochomatic transmitted response detector to generate a first transmitted response difference signal by comparing the output from said monochomatic transmitted response detector for each point of said first pattern with a known first transmitted response from each corresponding point on said second pattern to develop a first transmitted response difference signal;

a second transmitted response comparator coupled to said broadband transmitted response detector to generate a second transmitted response difference signal by comparing the output from said broadband transmitted response detector for each point of said first pattern with a known second transmitted response from each corresponding point of said second pattern to develop a second transmitted response difference signal; and a transmited difference map generator coupled to said first and second transmitted response comparators to receive said first and second transmitted response difference signals, respectively, to generate a transmitted difference map for said first pattern with values of said first and second transmitted difference signals the coordinates of said transmitted difference map for each point in said first pattern.

8. An inspection system as in claim 7 further comprising:

a post processor coupled to said reflected and transmitted difference map generators to receive said reflected and transmitted difference maps for said first pattern and to combine said reflected and transmitted difference maps into a combined difference map of said first pattern with four coordinates to unilaterally determine defects for said first pattern from said combined difference map.

9. An inspection system as in claim 8 wherein said post processor includes a subtractor to exclude regions of expected variation from said combined difference map of said first pattern to generate a defect map for said first pattern.

10. An inspection system as in claim 7 wherein said monochomatic probe emits a signal with a first frequency, said broadband probe emits a signal in a first band of frequencies, and said first frequency is outside said first band of frequencies.

11. An inspection system as in claim 7 wherein:

said monochomatic probe is directed to said first pattern on said first surface of said specimen at a low angle thereto;

said monochomatic reflected response detector receives darkfield images from said first surface on said specimen;

said monochomatic transmitted response detector receives darkfield images from said second surface on said specimen;

said broadband probe is directed to said first pattern on said first surface of said specimen in vicinity of perpendicular thereto;

said broadband reflected response detector receives brightfield images from said first surface of said specimen; and said broadband transmitted response detector receives brightfield images from said second surface of said specimen.

12. An inspection system as in claim 7 wherein:

said monochomatic probe is generated by a monochromatic light source;

said broadband probe is generated by a broadband light source;

said known first and second reflected responses of said second pattern are reflected darkfield and and brightfield responses, respectfully; and said known first and second transmitted responses of said second pattern are transmitted darkfield and brightfield responses, respectfully.

13. An inspection system as in claim 7 further comprising:

a first processor coupled to said reflected difference map generator to receive said difference map of said pattern to unilaterally determine defects for said first pattern from said reflected difference map; and a second processor coupled to said transmitted difference map generator to receive said transmitted difference map of said first pattern to unilaterally determine defects for said first pattern from said transmitted difference map.

14. An inspection system as in claim 13 wherein:

said first processor includes a first subtractor to exclude regions of expected variation from said reflected difference map of said first pattern to generate a reflected defect map for said first pattern; and said second processor includes a second subtractor to exclude regions of expected variation from said transmitted difference map of said first pattern to generate a transmitted defect map for said first pattern.

15. An inspection system to inspect a first pattern on a first surface of a specimen for defects against a second pattern that is intended to be the same, said inspection system comprising:

a monochomatic light source mounted opposite said first surface of said specimen to sequentially direct monochomatic light at a shallow angle to each point in said first pattern on said specimen;

a broadband light source mounted opposites first surface of said specimen to sequentially direct broadband light in vicinity of perpendicular to said each point in said first pattern on said specimen; and a darkfield response detector positioned to detect a darkfield response from each point of said first pattern on said specimen generated by said monochomatic light source;

a brightfield response detector positioned to detect a brightfield response from each point of said first pattern on said specimen generated by said broadband light source;

a darkfield response comparator coupled to said darkfield response detector to generate a darkfield difference signal by comparing the output from said darkfield response detector for each point of said first pattern with a known darkfield response from each corresponding point on said second pattern to develop a darkfield response difference signal;

a brightfield response comparator coupled to said brightfield response detector to generate a brightfield response difference signal by comparing the output from said brightfield response detector for each point of said first pattern with a known brightfield response from each corresponding point of said second pattern to develop a brightfield response difference signal; and a difference map generator coupled to said darkfield and brightfield response comparators to receive said darkfield and brightfield response difference signals, respectively, to generate a difference map for said first pattern with values of said darkfield and brightfield difference signals the coordinates of said difference map for each point in said first pattern.

16. An inspection system as in claim 15 wherein said darkfield light source probe emits a light beam with a first frequency, said brightfield light source emits a light beam with a first band of frequencies, and said first frequency is outside said first band of frequencies.

17. An inspection system as in claim 15 further comprising a processor coupled to said difference map generator to receive said difference map of said first pattern to unilaterally determine defects for said first pattern from said difference map.

18. An inspection system as in claim 17 wherein said processor includes a subtractor to exclude regions of expected variation from said difference map of said first pattern to generate a defect map for said first pattern.

19. An inspection system to inspect a first pattern on a transmissive specimen for defects against a second pattern that is intended to be the same, wherein said specimen has a first surface and a second surface substantially parallel to said first surface, said inspection system comprising:

a monochomatic light source mounted opposite said first surface of said specimen to sequentially direct monochromatic light at a shallow angle to each point in said first pattern on said first surface of said specimen;

a broadband light source mounted opposite said first surface of said specimen to sequentially direct broadband light in vicinity of perpendicular to said each point in said first pattern on said first surface of said specimen;

a darkfield reflected response detector positioned to detect a darkfield reflected response from each point of said first pattern on said first surface of said specimen generated by said monochomatic light source;

a brightfield reflected response detector positioned to detect a brightfield reflected response from each point of said first patterns on said first surface of said specimen generated by said broadband light source;

a darkfield transmitted response detector positioned opposite said second surface of said specimen to detect a darkfield transmitted response from each point of said first pattern on said second surface of said specimen generated by said monochomatic light source;

a brightfield transmitted response detector positioned opposite said second surface of said specimen to detect a brightfield transmitted response from each point of said first pattern on said second surface of said specimen generated by said broadband light source;

a darkfield reflected response comparator coupled to said darkfield reflected response detector to generate a darkfield reflected response difference signal by comparing the output from said darkfield reflected response detector for each point of said first pattern with a known darkfield reflected response from each corresponding point on said second pattern to develop a darkfield reflected response difference signal for said first pattern;

a brightfield reflected response comparator coupled to said brightfield reflected response detector to generate a brightfield reflected response difference signal by comparing the output from said darkfield reflected response detector for each point of said first pattern with a known brightfield reflected response from each corresponding point on said second pattern to develop a brightfield reflected response difference signal for said first pattern;

a reflected difference map generator coupled to said darkfield and brightfield reflected response comparators to receive said darkfield and brightfield reflected response difference signals, respectively, to generate a reflected difference map for said first pattern with values of said darkfield and brightfield reflected difference signals the coordinates of said reflected difference map for each point in said first pattern;

a darkfield transmitted response comparator coupled to said darkfield transmitted response detector to generate a darkfield transmitted response difference signal by comparing the output from said darkfield transmitted response detector for each point of said first pattern with a known darkfield transmitted response from each corresponding point on said second pattern to develop a darkfield transmitted response difference signal for said first pattern;

a brightfield transmitted response comparator coupled to said brightfield transmitted response detector to generate a brightfield transmited response difference signal by comparing the output from said brightfield transmitted response detector for each point of said first pattern with a known brightfield transmitted response from each corresponding point of said second pattern to develop a brightfield transmitted response difference signal for said first pattern; and a transmitted difference map generator coupled to said darkfield and brightfield transmitted response comparators to receive said darkfield and brightfield transmitted response difference signals, respectively, to generate a transmitted difference map for said first pattern with values said darkfield and brightfield transmitted difference signals the coordinates of said transmitted difference map for each point in said first pattern.

20. An inspection system as in claim 19 further comprising:

a post processor coupled to said reflected and transmitted difference map generators to receive said reflected and transmitted difference maps for said first pattern and to combine said reflected and transmitted difference maps into a combined difference map for said first pattern with four coordinates to unilaterally determine defects for said first pattern from said combined difference map.

21. An inspection system as in claim 20 wherein said post processor includes a subtractor to exclude regions of expected variation from said combined difference map of said first pattern to generate a defect map for said first pattern.

22. An inspection system as in claim 19 wherein said monochomatic light source emits a signal with a first frequency, said broadband light source emits a signal in a first band of frequencies, and said first frequency is outside said first band of frequencies.

23. An inspection system as in claim 19 further comprising:
- a first processor coupled to said reflected difference map generator to receive said reflected difference map of said first pattern to unilaterally determine defects for said first pattern from said reflected difference map; and
- a second processor coupled to said transmitted difference map generator to receive said transmitted difference map of said first pattern to unilaterally determine defects for said first pattern from said transmitted difference map.

24. An inspection system as in claim 23 wherein:
- said first processor includes a first subtractor to exclude regions of expected variation from said reflected difference map of said first pattern to generate a reflected defect map for said first pattern; and
- said second processor includes a second subtractor to exclude regions of expected variation from said transmitted difference map of said first pattern to generate a transmitted defect map for said first pattern.

* * * * *